US012747190B2

(12) United States Patent
Thankaraj et al.

(10) Patent No.: US 12,747,190 B2
(45) Date of Patent: Sep. 29, 2026

(54) HIGHLY DENSE RED MUD SHIELDS FOR X-RAY AND γ-RAY ATTENUATION

(71) Applicant: COUNCIL OF SCIENTIFIC & INDUSTRIAL RESEARCH, New Delhi (IN)

(72) Inventors: Salammal Shabi Thankaraj, Bhopal (IN); Deepti Mishra, Bhopal (IN); Sunil Kumar Sanghi, Bhopal (IN); Varsha Agrawal, Bhopal (IN); Rini Paulose, Bhopal (IN); Rahul Arya, Bhopal (IN); Sriram Sathaiah, Bhopal (IN); Sanjai Kumar Singh Rathore, Bhopal (IN); Avanish Kumar Srivastava, Bhopal (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 733 days.

(21) Appl. No.: 18/245,062

(22) PCT Filed: Sep. 10, 2021

(86) PCT No.: PCT/IN2021/050888
§ 371 (c)(1),
(2) Date: Mar. 13, 2023

(87) PCT Pub. No.: WO2022/054094
PCT Pub. Date: Mar. 17, 2022

(65) Prior Publication Data

US 2024/0018050 A1 Jan. 18, 2024

(30) Foreign Application Priority Data

Sep. 14, 2020 (IN) ............................ 202011039832

(51) Int. Cl.
*C04B 33/132* (2006.01)
*C04B 33/32* (2006.01)
(Continued)

(52) U.S. Cl.
CPC ........ *C04B 33/1322* (2013.01); *C04B 33/323* (2013.01); *C04B 33/326* (2013.01);
(Continued)

(58) Field of Classification Search
CPC ............. C04B 33/1322; C04B 33/323; C04B 33/326; C04B 35/01; C04B 35/453;
(Continued)

(56) References Cited

U.S. PATENT DOCUMENTS 3,886,244 A * 5/1975 Bayer ................. C04B 33/1322 264/44
4,368,273 A * 1/1983 Puskas ................ C04B 18/0409 501/155

(Continued)

FOREIGN PATENT DOCUMENTS

CN 101805208 * 8/2010
CN 106631150 * 5/2017

(Continued)

OTHER PUBLICATIONS

Amritphale et al., A novel process for making radiopaque materials using bauxite—Red Mud, Journal of the European Ceramic Society, 27(2007) 1945-1951 (Year: 2007).*

(Continued)

*Primary Examiner* — Cephia D Toomer
(74) *Attorney, Agent, or Firm* — DINSMORE & SHOHL LLP

(57) ABSTRACT

A novel eco-friendly method has been developed for the fabrication of high dense (3.3-5.2 g/cc) red mud based material blocks for shielding high energy X- and γ-rays. The
(Continued)

red mud based material blocks with various densities were fabricated by hot compacting partially melted red mud, red mud:$Bi_2O_3$, red mud:$Ba(OH)_2$ and red mud:$Bi_2O_3$:$Ba(OH)_2$ samples at 1150° C., 1000° C., 1050° C. and 1000° C., respectively. This material can be used to build radiation shielding structures in medical diagnosis, radiotherapy, industrial radiography, particle accelerators, food sterilization plants, nuclear power plants, and radioactive material storage rooms, without further structural support unlike lead (concrete walls). It is economically viable and will suppress the accumulation of hazardous red mud and associated environmental pollutions.

13 Claims, 3 Drawing Sheets

(51) Int. Cl.

| | |
|---|---|
| ***C04B 35/01*** | (2006.01) |
| ***C04B 35/453*** | (2006.01) |
| ***C04B 35/626*** | (2006.01) |
| ***G21F 1/08*** | (2006.01) |
| *A61B 6/10* | (2006.01) |

(52) U.S. Cl.
CPC ............ *C04B 35/01* (2013.01); *C04B 35/453* (2013.01); *C04B 35/6261* (2013.01); *G21F 1/085* (2013.01); *A61B 6/107* (2013.01); *C04B 2235/3215* (2013.01); *C04B 2235/3298* (2013.01); *C04B 2235/6562* (2013.01); *C04B 2235/6565* (2013.01); *C04B 2235/6567* (2013.01); *C04B 2235/77* (2013.01); *C04B 2235/96* (2013.01)

(58) Field of Classification Search
CPC ........ C04B 35/6261; C04B 2235/3215; C04B 2235/3298; C04B 2235/6562; C04B 2235/6565; C04B 2235/6567; C04B 2235/77; C04B 2235/96; C04B 35/645; C04B 2235/3272; C04B 2235/349; C04B 2235/44; C04B 2235/668; C04B 2235/80; C04B 33/32; G21F 1/085; G21F 1/08; A61B 6/107; C01F 7/066; A61N 2005/1094
See application file for complete search history.

(56) References Cited

U.S. PATENT DOCUMENTS

| | | | |
|---|---|---|---|
| 8,816,309 | B1 | 8/2014 | Struthers et al. |
| 9,708,221 | B2 | 7/2017 | Miyao et al. |
| 10,026,513 | B2 | 7/2018 | Cardon et al. |
| 2006/0066013 | A1 | 3/2006 | Amritphale et al. |
| 2020/0239355 | A1 | 7/2020 | Naito et al. |

FOREIGN PATENT DOCUMENTS

| | | | |
|---|---|---|---|
| CN | 113409979 | * | 9/2020 |
| IN | 201911033448 | A1 | 8/2021 |
| WO | 2016202291 | A1 | 12/2016 |
| WO | 2017038378 | A1 | 3/2017 |

OTHER PUBLICATIONS

Mori, et al., "Iron (III) Oxide-Based Ceramic Material for Radiation Shielding", Ceramics, vol. 3, pp. 258-264, 2020.
Baalamurugan, et al., "Utilization of induction furnace steel slag in concrete as coarse aggregate for gamma radiation shielding", Journal of Hazardous Materials, vol. 369, pp. 561-568, 2019.
Chauhan, et al., "Development and Design Mix of Radiation Shielding Concrete for Gamma-ray Shielding", J. Inorg. Organomet Polym., vol. 27, pp. 871-882, 2017.
Chen, et al., "Novel light-weight materials for shielding gamma ray", Radiation Physics and Chemistry, vol. 96, pp. 27-37, 2014.
Chen, "Investigating of Barite Shielding Boards for Radiation Protection", 3rd International Conference on Green Materials and Environmental Engineering, pp. 1-5, 2017.
Han, et al., "Smart and Multifunctional Concrete Toward Sustainable", Chapter 19 Radiation Shielding Concrete, pp. 329-337, 2017.
Jawad, et al., "Radiation shielding properties of some ceramic wasted samples", International Journal of Environmental Science and Technology, pp. 1-4, 2019.
Durkee III, et al., "High Density Composites Replace Lead", Economic Technologies, pp. 1-7, 2005.

* cited by examiner

HIGHLY DENSE RED MUD SHIELDS FOR X-RAY AND γ-RAY ATTENUATION

CROSS REFERENCES TO RELATED APPLICATIONS

This application is a national-stage application under 35 U.S.C. § 371 of International Application No. PCT/IN2021/050888, filed Sep. 10, 2021, which International Application claims benefit of priority to Indian Patent Application number 202011039832, filed Sep. 14, 2020.

FIELD OF THE INVENTION

The present invention relates to a high dense red mud shields for X- and γ-ray attenuation. The present invention also relates to a novel eco-friendly method for the fabrication of high dense (3.2-5.2 g/cc) red mud (hazardous alumina industrial waste) based material blocks for shielding high energy X- and γ-rays.

BACKGROUND OF THE INVENTION

Radiation shielding materials are integral part of building construction in X-ray diagnosis, radiotherapy, particle accelerators, food sterilization plants, nuclear power plants, radioactive nuclide storage rooms, etc. Lead and heavy weight concretes are commonly used as a structural material to shield high energy X- and gamma-rays. Among that, lead is widely used to shield X- and γ-rays due to its high atomic number (82), density (11.2 g/cc) and comparatively low cost. However, lead is carcinogenic and listed as a top second hazardous material. So, the usage of lead has been discouraged by most of the countries. Apart from lead, light weight (<2.4 g/cc) and heavy weight concretes (>2.4 g/cc) are also used to build radiations shielding structures. The heavy weight concretes are commonly fabricated by replacing 70-80 wt % of aggregates with iron shot, iron ores (magnetite, limonite, hematite, etc.), barite, lead shot, etc. Concrete is thermally unstable and occupies huge useful space. It tends to crack and loses its strength when the temperature goes above 300° C. due to the breakage of calcium-silicate-hydrate gel. Further the process of production of cement, which is used in concrete, is energy intensive and is associated with global warming due to release of $CO_2$ during the calcinations of limestone. The cost of heavy weight concrete will increase exponentially, when the density of the concrete goes above 3.3 g/cc due to the raw material cost as well as the increased farm pressure and wear and tear of the equipments. It will also consume natural resources and increases primary mining.

Reference can be made to the Indian patent application no. 201911033448, titled "Lead Free Red Mud Based X-ray Shielding Tile" filed by Shabi Thankaraj Salammal et al, wherein red mud, $BaSO_4$/$Bi_2O_3$ and kaolin clay/sodium hexametaphosphate (SHMP) were used to fabricate X-ray shielding tiles through ceramic route. The tiles were fabricated using 45 wt % of red mud and 45 wt % of $Bi_2O_3$/$BaSO_4$ and 10 wt % of SHMP/kaolin clay binder. The above mixtures were wet grinded and then green tiles were fabricated by applying ≈53.14 MPa pressure. The tiles were sintered between 900-1200° C. to get sufficient strength. The 6.3 mm and 11.7 mm thick red mud:$Bi_2O_3$:kaoline clay tile and red mud:$BaSO_4$:kaoline clay tile, respectively, possess the attenuation equivalent to 2 mm lead at 140 kVp. The red mud:$Bi_2O_3$:kaoline clay and red mud:$BaSO_4$:kaoline clay tiles achieved density of only 3.41 g/cc and 2.35 g/cc, respectively even after the addition of 45 wt % of high Z materials. This is due to the formation of pores during ceramic processing. So, it requires quite thick wall to shield gamma and industrial X-rays.

Reference may be made to the U.S. Pat. No. 7,524,452B2 titled "Low Temperature Process for Making Radiopac Materials Utilizing Industrial/Agricultural Waste as Raw Material", by S. S. Amritphale et al" wherein industrial waste like fly ash, red mud and rice husk has been used to fabricate radiation shielding tiles together with barium carbonate ($BaCO_3$) as high Z metal compound. The tiles were fabricated through ceramic route by sintering between 920° C. till 1300° C. It is worth to point out here that the attenuation of high energy photons are directly related to the atomic number of the shielding materials and their density. The main drawback of this patent is the use of fly ash and rice husk which are rich in low Z elements like $SiO_2$ and $Al_2O_3$. Eventually, the 10 mm thick sample was reported to attenuate 66% of the 150 keV X-ray beams (HVL (Half-value layer) is 6.8 mm). It requires thick slab of about 6" thickness for the construction of X-ray diagnostic and CT scanner room to provide adequate shielding against X-ray photons. Apart from that, $BaCO_3$ will decompose at ≈1000° C. into BaO and $CO_2$, which is a green house gas responsible for global warming.

Reference can be made to the article "Development and Design Mix of Radiation Shielding Concrete for Gamma-ray Shielding", J. Inorg Organomet Polym 27 (2017) 871-882, authored by R. K. Chauhan et al., wherein red mud, $BaSO_4$ and carbon powders were used as precursors to fabricate radiation shielding aggregates. The synthetic radiation shielding aggregates were made by adding 10 wt % $BaSO_4$, 5 wt % carbon powder with red mud. Small balls were made using those mixtures and then sintered at 1300° C. for the duration of two hours to promote the formation of various barium phases. The aggregates were then crushed into less than 20 mm sized small aggregates and concretes were made using ordinary portland cement as per standard procedure. The density of the concrete was 3.3 g/cc. The gamma ray attenuation (Cs-137 (0.662 MeV)) characteristics of the developed blocks were found to be slightly higher than the hematite ore based concrete. However, during sintering, $Fe_2O_3$ will be reduced in presence of carbon powder and will release $CO_2$, as well as the $BaSO_4$ will decompose and emit $SO_2$. Both are non-environmental friendly. Moreover, such cement matrixes are thermally unstable and will occupy huge space.

Reference can be made to the article entitled "Radiation shielding properties of some ceramic wasted samples" International Journal of Environmental Science and Technology, 16 (2019) 5039-5042 authored by A. A. Jawad et al., wherein four various types of muds like kutahya tile mud, red mud, white mud and white casting mud were used to fabricate gamma ray shielding material through ceramic route by sintering between 950° C. till 1040° C. Among all, the kutahya tile mud posses the highest attenuation. The HVL of the kutahya tile mud is ≈73 mm at 1.332 MeV (Cobalt-60 source). The HVL of red mud sample is 80 mm at 1.332 MeV, which is higher than the concrete and other red mud based shields. Eventually, it requires quite thick wall to shield gamma rays and will occupy huge useful space.

Reference can be made to the article entitled "Novel light-weight materials for shielding gamma ray" Radiation Physics and Chemistry 96(2014) 27-37, authored by Shuo Chen et al, whereas steel-steel composite metal foams, aluminium steel composite metal foams, aluminum A356, open-cell aluminium foam paraffin wax sandwich composite, open-cell aluminium foam borated polyethylene sandwich composite, open-cell aluminium foam water sandwich composites were fabricated and their gamma ray attenuation characteristics were studied using Cobalt 60 and Caesium 137 sources. The steel-steel composite foam possesses attenuation of Al356 at 1.332 Mev (i.e. 37 mm thick steel-steel composite sample attenuates ≈40% of 1.332 MeV photons). Although steel has more high Z elements than AI 356, it possesses poor attenuation than Al356 due to the presence of pores, which is detrimental for the attenuation of high energy photons. Although the foams are light, but they demand very thick wall to shield such high energy photons and will occupy huge useful space.

Reference can be made to the article entitled "Utilization of induction furnace steel slag in concrete as coarse aggregate for gamma radiation shielding" authored by J. Baalamurugan et al, wherein 2.81 g/cc concrete was fabricated by replacing 50% of the aggregates with Induction Furnace (IF) steel slag in concrete matrix. The developed block posses the compressive strength of 29 MPa. The half value layer of the developed concrete was 31 mm for Cobalt 60, which is slightly less than the conventional concrete (35.5 mm) fabricated by them. However, they used cement matrix, which is thermally unstable and will occupy huge space.

Reference can be made to the PCT publication WO2016202291A1 entitled "Shielding material for shielding radioactive ray and preparation method thereof" authored by Chang Ming-chuan et al., whereas 3.46 till 3.55 g/cc radiation shielding concretes were made using Portland cement, fine aggregate (less than 4.75 mm borosilicate glass and barite sand), coarse aggregate (greater than 4.75 mm lead stone and barite) and other admixtures. The developed concrete posses the density between 3.46 till 3.55 g/cc even after the addition of 71-75% $BaSO_4$. Moreover, it contains lead, which is toxic. Such cement matrixes are not thermally stable.

Reference may be made to the book entitled "Smart and Multifunctional Concrete Toward Sustainable Infrastructures" authored by Baoguo Han et al, ISBN978-981-10-4348-2, publisher, Springer Nature Singapore Pte Ltd. 2017, Chapter 19 "Radiation Shielding Concrete" authors Baoguo Han et al., wherein it is reported that the radiation shielding concretes are made by incorporating 70-80% of high density aggregates such as barite, hematite, ilmenite, boron (shielding neutrons), etc. The drawbacks of the developed concrete is their radiation instability. It is thermally unstable, resulting in cracks due to shrinkage/expansion of aggregates and evaporation of crystal water from the concrete. The concrete tends to lose its strength above 200° C. The cost of the concrete increases tremendously when the density of concrete goes above 3.8 g/cc due to the wearing of equipments and extreme farm pressure.

Reference can be made to the article "investigation of barite shielding boards for radiation protection", 2017 3$^{rd}$ International Conference on Green Materials and Environmental Engineering (GMEE 2017), ISBN: 978-1-60595-500-1, authored by Tzong-Jer Chen, wherein three various barite shielding boards (BSB) were developed by sandwiching the 15, 25 and 37 mm thick radiation shielding concrete between 5 mm thick fiber concrete. The BSB radiation shielding layer was made using 80% of <3 mm and 20%<75 μm sized barite aggregates. The Portland cement was used with the w/c ratio of 0.36. The density of the shield was 3.4 g/cc. 15 mm thick shield posses the attenuation characteristics of 2 mm lead. It will require quite thick wall to shield high energy gamma rays.

Reference can be made to U.S. Pat. No. 9,708,221 titled "Brick, Tile, Floorboard, Ceiling Panel, and Roofing Material and Method for Manufacturing Same" filed by Yasumichi Miyao et al., where in various structures of X- and γ-ray shielding materials like bricks, panels, roofing material, etc., have been fabricated using hematite ($Fe_2O_3$). Nearly 85-100 wt % of 0.3 to 800 μm sized $Fe_2O_3$ particles were mixed with kaolinite ($AlSiO_3(OH)_4$) to improve the mouldability of the material. The precursor were then molded into desired shapes like block, brick, cylinder, thick plate, etc., depends on the application by applying high pressure (maximum of 112 MPa). The molded articles were then fired between 1280° C. for 120 hrs. The bulk density of the fired molded article is 2.8 g/cc, which is very less even after the addition of 90 wt % $Fe_2O_3$. Moreover, the process is energy intensive due to long firing time.

Reference can be made to the article entitled "Iron (III) Oxide-Based Ceramic Material for Radiation Shielding" Ceramics, 3(2020) 258-264 authored by Hiroyuki Mori et al, whereas $Fe_2O_3$ bricks were fabricated using nearly 99% $Fe_2O_3$ powder purified from the steel industry waste. The developed bricks posses the specific gravity and compressive strength of 4.9 and 200 MPa, respectively. The developed bricks posses 40% of the attenuation of lead. The HVL of the bricks at 1.332 MeV (Co-60 source) is 25 mm. It consumes 99% of $Fe_2O_3$, which can be easily recycled. It requires more space than the red mud based materials.

Reference may be made to the U.S. Pat. No. 8,816,309 titled "Radiation Shielding Panel, filed by Clayton W. Struthers et al" wherein radiation shielding polymer panels were fabricated by incorporating tungsten powder in polyurea matrix. In particular, 80, 15, and 5 wt % of tungsten powders of having dimensions like 90, 9, and 0.9 microns, respectively, were loaded in the polyurea matrix. The 90 micron sized particle form base layer and then the 9 micron particle was reported to form another layer on top of it. The 0.9 micron particles were diffused into both the layers and filled the gap between the larger particles. The main drawback of such polymer based radiation shielding materials are their poor mechanical and thermal stability and durability. The polymers tend to decompose during continuous irradiation. Further the nanoparticles are expensive, which suppresses their wide application spectrum.

Reference may be made to the report entitled "High Density Composites Replace Lead" Ecomass technologies, authored by Robert R. Durkee, wherein polymer-metal composites have been fabricated by incorporating various nanoparticles like tungsten, barium ferrite, carbonyl iron, barium sulfate, stainless steel and cooper in various polymers like polyamides, polyurethanes, polyethylenes, polymethylpentenes, polysulfones, etc. The polymer-metal nanocomposites having density ranging from 2.5-11 g/cc were fabricated by varying the raw material composition. They are non-toxic and possesses good attenuation characteristics as well. The main drawbacks of such polymer based radiation shielding materials are their poor mechanical and thermal stability and durability when exposed to continuous ionizing radiations. In particular, the polymer backbones tend to break due to the formation of free radicals upon irradiation. Further, most of the high Z elements are expensive and it increases the production cost as well.

Reference can be made to the U.S. Ser. No. 10/026,513 entitled "Radiation shielding and processes for producing and using the same" filed Joseph M. Cardon et al, whereas optically transparent bismuth-polymer compound was developed through polymerization of organobismuth monomer compound by mixing with a co-monomer and a crosslinking agent. The developed shielding material contains 30-40 wt % of bismuth. The polymers are thermally not stable and expensive. The polymers tend to decompose when exposed to high energy radiation. They are suitable for making aprons, curtains, etc.

From the above there are many issues in the art. Historically, Lead has been widely used as X- and gamma-ray shielding material due to its high atomic number (82), density (11.35 g/cc) and comparatively low cost. But lead is carcinogenic and it is reported to be a top second hazardous element. So, the usage of lead is discouraged by most of the countries. Such radiation shielding structures are reported to harm the public as well as the operating personal through contact as well as the formation of lead dust. The red mud based X-ray shielding tiles fabricated through ceramic route possesses density of 3.4 g/cc and 2.35 g/cc even after the addition of 45 wt % of $Bi_2O_3$ and $BaSO_4$, respectively due to the formation of pores. It needs quite thick wall to attenuate the gamma and industrial X-rays (>150 kVp) and will occupy huge useful space.

In some red mud based radiation shielding materials; $BaCO_3$, $BaSO_4$ and coke were used as high Z metal compound along with red mud and sintered at 1300° C. to form bafertisite and other barium based high dense phases. At such elevated temperatures, both the $BaCO_3$ and $BaSO_4$ will decompose and releases non-environmental friendly gases like $CO_2$ and $SO_2$, which is not appreciable.

In addition to lead, heavy weight and light weight concretes are also used to shield high energy photons. The main drawback of concrete is that, it is not thermally stable. The concrete will start to lose its strength when the temperature goes above 200° C. The concretes are reported to decrease its strength by 40%, when the temperature goes beyond 350° C. Such decrease in strength occurred due to the evaporation of crystal water and the decomposition of calcium-silicate-hydrate (C-S-H) gel. The concretes tend to crack when the temperature goes above 400° C., which is detrimental for radiation attenuation. Moreover, portland cement matrices requires twenty eight days of water curing to ensure proper matrix formation which is time as well as water consuming. The heavy weight concretes will consume non-replenishable natural resources and expensive.

Various nano and micro particles of heavy metal compounds like bismuth, tungsten, barium, iron, etc., are used to incorporate in polymer matrix to fabricate flexible polymer-metal composites for shielding X- and gamma-rays. The polymers are thermally and mechanically unstable and result in poor durability when it is exposed to continuous ionizing radiations due to the formation of free radicals. They may degrade when exposed to organic solvents. Further these materials are expensive and economically not viable. They are suitable for making aprons, thyroid shield, gonad shield, etc.

Therefore, there is a need in the art for a highly dense and lead free radiation shielding material and an environmental friendly method for preparing the same.

Objectives of the Invention

The main objective of the present invention is to provide a lead free red mud based X- and gamma-ray shielding material through a novel green and eco-friendly method.

Another objective of the present invention is to provide a methodology for the conversion of hazardous iron rich red mud into X- and gamma-ray shield instead of using iron ores like magnetite, hematite, limonite, iron shot, lead shot, etc., as high dense aggregates.

Still another objective of the present invention is to improve the density of red mud based materials by closing the pores through hot compaction and thereby to increase both the X- and gamma-ray attenuation as well as the mechanical strength.

Yet another objective of the present invention is to improve the density of the red mud shield by adding $Bi_2O_3$ and $Ba(OH)_2$ with red mud and by promoting the crystallization of high dense phases like $Bi_{12}SiO_{20}$, $2BiFeO_3$, $BaTiO_3$, and $BaFe_{12}O_{19}$, by optimizing the sintering temperatures.

Still another objective of the present invention is to reduce the thickness of the radiation shield and thereby to increase the usable area of the rooms wherever radioactive sources are used.

Still another objective of the present invention is to fabricate mechanically compatible radiation shield to build the radiation shielding structure without further structural support like lead.

Still another objective is to find an economically viable alternative for shielding X- and gamma-rays instead of conventionally used toxic lead using industrial waste as a major raw material.

Yet another objective is to promote the large scale utilization of hazardous red mud and thereby to reduce the environmental pollution and primary mining.

SUMMARY OF THE INVENTION

An aspect of the present invention provides a red mud based material for X- and γ-ray attenuation comprising:

a) 50-100 wt % of red mud; and b) 0 to 50 wt % of $Bi_2O_3$ or $Ba(OH)_2$ or a mixture of $Bi_2O_3$ and $Ba(OH)_2$ (50:50 wt %).

In another aspect of the present invention, there is provided a red mud based material, wherein the density of said material is in the range from 3.3 g/cc to 5.23 g/cc.

In still another aspect of the present invention, there is provided a red mud based material, wherein the density of red mud, red mud:$Bi_2O_3$, red mud:$Ba(OH)_2$ and red mud:$Bi_2O_3$:$Ba(OH)_2$ shields are 3.3 g/cc, 5.23 g/cc, 4.6 g/cc and 4.7 g/cc, respectively.

In yet another aspect of the present invention, there is provided a red mud based material, wherein the compressive strength of the material is in the range from 34 MPa to 282.15 MPa.

In another aspect of the present invention, there is provided a red mud based material, wherein the compressive strength of red mud, red mud:$Bi_2O_3$, red mud:$Ba(OH)_2$ and red mud:$Bi_2O_3$:$Ba(OH)_2$ are 38.18 MPa, 282.15 MPa, 144 MPa and 122 MPa, respectively.

In still another aspect of the present invention, there is provided a red mud based material, wherein half value layer of the material is in the range of 20.96 mm to 34 mm at 1.33 MeV ($^{60}Co$ source).

In another aspect of the present invention, there is provided a red mud based material, wherein half value layer of the material at 150 kVp X-ray is in the range from 0.7434 mm to 3.1 mm.

Another aspect of the present invention provides a process for preparation of a red mud based material for X- and γ-ray attenuation comprising:

a. taking 50-100 wt % of red mud;

b. separately taking 0 to 50 wt % of $Bi_2O_3$ or $Ba(OH)_2$ or a mixture of $Bi_2O_3$ and $Ba(OH)_2$ (50:50 wt %);

c. grinding the red mud in a ball mill for 4 hrs;

d. adding $Bi_2O_3$ or $Ba(OH)_2$ or a mixture of $Bi_2O_3$ and $Ba(OH)_2$ to said ball mill of step (c) and grinding for one more hour to obtain a mixture;
e. taking the mixture obtained in step (d) in a graphite die and sintering at a temperature in the range of 1000° C. to 1050° C. in a hot press at a heating rate of 7° C./min to obtain a partially melted mixture;
f. compacting the partially melted mixture obtained in step (e) by applying pressure in the range of 23 MPa to 40 MPa for 30-60 seconds; and cooling at a rate of 10° C./minutes to 27° C. to obtain the red mud based material.

In another aspect of the present invention, there is provided a process for preparation of a red mud based material, wherein the heating step results in formation of high dense phases like $Fe_3O_4$, hematite, cancrinite, nepheline, pseudobrookite, gehlenite, silico-ferrite of calcium and aluminum (SFCA), $Bi_{12}SiO_{20}$, $2BiFeO_3$, $BaTiO_3$, and $BaFe_{12}O_{19}$.

DETAIL DESCRIPTION OF THE INVENTION

Figure 1:
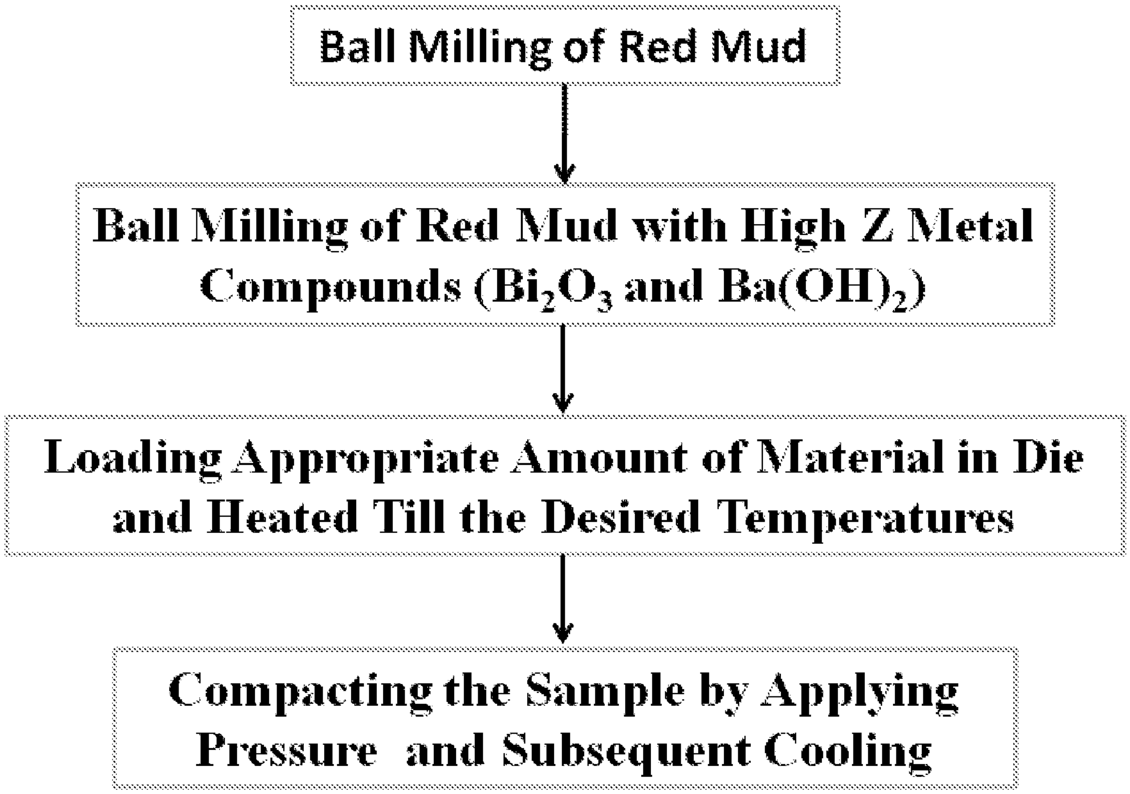
FIG. 1: Depicts the flow chart for the fabrication of high dense red mud based blocks for radiation shielding.

Accordingly the present invention provides a red mud based material for X- and gamma-ray attenuation which comprises of raw materials like red mud, $Bi_2O_3$ and $Ba(OH)_2$ in which red mud is initially ball milled for a duration of 4 hrs using 350 gm stainless steel balls (6 Nos) and then equal amount of $Bi_2O_3$ or $Ba(OH)_2$ or $Bi_2O_3$:Ba $(OH)_2$ (50:50 ratio) is added with the grinded red mud and then ball milled for another 1 hr to obtain a uniform mixture, then the mixture is taken in a 5 cm die and loaded into the furnace and heated between 1000° C. to 1150° C. at a rate of 7° C./min. Then pressure in the range of 23 MPa to 40 MPa is applied in a hot press to the partially melted mixture at the end of dwelling period and the compressed mixture is cooled at a rate of 10° C./min to fabricate blocks.

In an embodiment of the present invention, the raw materials used for the preparation of X- and γ-rays shielding blocks are red mud, $Bi_2O_3$ and $Ba(OH)_2$.

In another embodiment of the present invention, pure red mud is grinded in a ball mill for 4 hrs to crush them into fine powders using 350 gm stainless steel balls (6 Nos).

In yet another embodiment of the present invention, grinded red mud is mixed with commercial grade 50 wt % of $Bi_2O_3$ or $Ba(OH)_2$ or a mixture of $Bi_2O_3$ and $Ba(OH)_2$ (50:50 ratio) and then both are together grinded in a ball mill for 1 hr.

In still another embodiment of the present invention, an amount of the red mud or red mud:$Bi_2O_3$ or red mud:Ba $(OH)_2$ or red mud:$Bi_2O_3$:$Ba(OH)_2$ with respect to the desired thickness is taken in a die and then loaded into the hot press.

In still another embodiment of the present invention, the red mud, red mud:$Bi_2O_3$, red mud:$Ba(OH)_2$ and red mud: $Bi_2O_3$:$Ba(OH)_2$ samples are heated to 1150° C., 1000° C., 1050° C. and 1000° C., respectively in a hot press with a heating rate of 7° C./min.

In yet another embodiment of the present invention, the partially melted red mud, red mud:$Bi_2O_3$, red mud:$Ba(OH)_2$ and red mud:$Bi_2O_3$:$Ba(OH)_2$ samples are compacted by applying 23.4 MPa, 40 MPa, 23.4 MPa and 40 MPa pressure, respectively in a hot press at the end of the dwelling period.

In yet another embodiment of the present invention, the boehmite, goethite, gibbsite and calcite present in the red mud decomposes during sintering and form new phases like hematite, cancrinite, nepheline, pseudobrookite, gehlenite, perovskite, silico-ferrite of calcium and aluminium (SFCA), $Bi_{12}SiO_{20}$, $2BiFeO_3$, $BaTiO_3$, and $BaFe_{12}O_{19}$.

In yet another embodiment of the present invention, the developed blocks were tested for density, porosity, X-ray diffraction, heavy element leaching, X-ray (150 kVp) and gamma ray attenuation (Cobalt-60) analysis.

An embodiment of the present invention provides a red mud based material for X- and γ-ray attenuation comprising:
a) 50-100 wt % of red mud; and
b) 0 to 50 wt % of $Bi_2O_3$ or $Ba(OH)_2$ or a mixture of $Bi_2O_3$ and $Ba(OH)_2$ (50:50 wt %).

In another embodiment of the present invention, there is provided a red mud based material, wherein the density of said material is in the range from 3.3 g/cc to 5.23 g/cc.

In still another embodiment of the present invention, there is provided a red mud based material, wherein the density of red mud, red mud:$Bi_2O_3$, red mud:$Ba(OH)_2$ and red mud: $Bi_2O_3$:$Ba(OH)_2$ shields are 3.3 gcc, 5.23 g/cc, 4.6 g/cc and 4.7 g/cc, respectively.

In yet another embodiment of the present invention, there is provided a red mud based material, wherein the compressive strength of the material is in the range from 34.18 MPa to 282.15 MPa.

In another embodiment of the present invention, there is provided a red mud based material, wherein the compressive strength of red mud, red mud:$Bi_2O_3$, red mud:$Ba(OH)_2$ and red mud:$Bi_2O_3$:$Ba(OH)_2$ are 34.18 MPa, 282.15 MPa, 144 MPa and 122 MPa, respectively.

In still another embodiment of the present invention, there is provided a red mud based material, wherein half value layer of the material is in the range of 20.96 mm to 34.02 mm at 1.33 MeV ($^{60}Co$ source).

In another embodiment of the present invention, there is provided a red mud based material, wherein half value layer of the material at 150 kVp X-ray is in the range from 0.7434 mm to 3.10 mm.

Another embodiment of the present invention provides a process for preparation of a mud based material for X- and γ-ray attenuation comprising:
a. taking 50-100 wt % of red mud;
b. separately taking 0 to 50 wt % of $Bi_2O_3$ or $Ba(OH)_2$ or a mixture of $Bi_2O_3$ and $Ba(OH)_2$ (50:50 wt %);
c. grinding the red mud in a ball mill for 4 hrs;
d. adding $Bi_2O_3$ or $Ba(OH)_2$ or a mixture of $Bi_2O_3$ and $Ba(OH)_2$ to said ball mill of step (c) and grinding for one more hour to obtain a mixture;
e. taking the mixture obtained in step (d) in a graphite die and sintering at a temperature in the range of 1000° C. to 1150° C. in a hot press at a heating rate of 7° C./min to obtain a partially melted mixture;
f. compacting the partially melted mixture obtained in step (e) by applying pressure in the range of 23 MPa to 40 MPa for 30-60 seconds; and cooling at a rate of 10° C./minutes to 27° C. to obtain the red mud based material.

In another embodiment of the present invention, there is provided a process for preparation of a mud based material, wherein the heating step results in formation of high dense phases like $Fe_3O_4$, hematite, cancrinite, nepheline, pseudo-brookite, gehlenite, silico-ferrite of calcium and aluminum (SFCA), $Bi_{12}SiO_{20}$, $2BiFeO_3$, $BaTiO_3$, and $BaFe_{12}O_{19}$.

The novelty of the present invention in the fact that the process of the present invention obviates the drawbacks of the existing red mud based radiation shielding materials mainly on the density and half value layer of the radiation shields.

In this present investigation, the inventors have compacted a partially melted red mud, red mud:$Bi_2O_3$, red mud:$Ba(OH)_2$ and red mud:$Bi_2O_3$:$Ba(OH)_2$ samples close to their melting point to close the pores and thereby to increase the density. The density of red mud, red mud:$Bi_2O_3$, red mud:$Ba(OH)_2$ and red mud:$Bi_2O_3$:$Ba(OH)_2$ blocks are 3.3 g/cc, 5.23 g/cc, 4.6 g/cc and 4.7 g/cc, respectively. The porosity of the developed red mud, red mud:$Bi_2O_3$, red mud:$Ba(OH)_2$ and red mud:$Bi_2O_3$:$Ba(OH)_2$ blocks are 3.8%, 2.8%, 0.08% and 2.0%, respectively. The half value layer of red mud, red mud:$Bi_2O_3$, red mud:$Ba(OH)_2$ and red mud:$Bi_2O_3$:$Ba(OH)_2$ samples at 1.33 MeV are 34.02 mm, 20.96 mm, 26.80 mm and 24.0 mm, respectively. The HVL of developed red mud:$Bi_2O_3$ block is more than half of lead (HVL of lead at 1.33 MeV is 12.5 mm) and three times smaller than the concrete (HVL of concrete at 1.33 MeV is 60.5 mm). The HVL of the sample at 150 kVp is 3.10 mm, 0.743 mm, 1.0754 mm and 0.8776 mm for red mud, red mud:$Bi_2O_3$, red mud:$Ba(OH)_2$ and red mud:$Bi_2O_3$:$Ba(OH)_2$ sample, respectively. Moreover, the developed material is lead free and the process is green as it does not emit any green house gases like $CO_2$ and $SO_2$ during sintering. The developed material possess the compressive strength between 34 MPa-282 MPa, which is suitable for building the radiation shielding structures without additional structural support like lead. It eventually decreases the thickness of the radiation shield and increases the usable spaces.

In the process of the present invention, high dense and lead free radiation shielding materials have been developed using iron rich red mud (alumina industrial waste), $Ba(OH)_2$ and $Bi_2O_3$. The developed radiation shielding materials can be used to shield both the X- and gamma-rays that come out of X-ray diagnostic, radio therapy rooms, food sterilization plants, radioactive material storage rooms, industrial radiography, particle accelerators, and nuclear power plants. The 301.82 mm thick block possesses (red mud:$Bi_2O_3$) the attenuation equivalent to 180 mm lead at 1.33 MeV, and 6.20 mm thick pellet possess the attenuation equivalent to 2.5 mm lead at 150 kVp. The developed material possesses sufficient strength (34-282 MPa depending on the composition), which is suitable for structural applications. The material eventually requires much less thickness as compared to polymer-metal composites, heavy weight concrete, barite board, and light weight concrete based radiations shields. Moreover, the developed blocks can be directly used to build radiation shielding structure without further structural support unlike lead. It is economically viable and will suppress the accumulation of hazardous red mud and associated environmental pollutions.

The red mud blocks with various densities were fabricated by hot compacting partially melted red mud, red mud:$Bi_2O_3$, red mud:$Ba(OH)_2$ and red mud:$Bi_2O_3$:$Ba(OH)_2$ samples at 1150° C., 1000° C., 1050° C. and 1000° C., respectively. The red mud is grinded in a ball mill and then mixed with appropriate weight percentage of high Z metal compound. The compound mixture is taken in a die and then heated to a desired temperature at a heating rate of 7° C./min. The partially melted powder is compacted by applying pressures between 23-40 MPa for few seconds and then the samples are cooled at a rate of 10° C./min. The densities of the developed blocks of red mud, red mud:$Bi_2O_3$, red mud:Ba $(OH)_2$ and red mud:$Bi_2O_3$:$Ba(OH)_2$ samples are found to be 3.3 g/cc, 5.2 g/cc, 4.6 g/cc, and 4.7 g/cc, respectively. Gamma attenuation characteristics of the developed shields are studied using Cobalt 60 source by varying the thickness of the shield. The HVL of the sample at 1.33 MeV photon is 34.02 mm, 20.96 mm, 26.80 mm and 24 mm for red mud, red mud:$Bi_2O_3$, red mud:$Ba(OH)_2$ and red mud:$Bi_2O_3$:Ba $(OH)_2$ sample, respectively. The 489.88 mm, 301.82 mm, 385.92 and 345.6 mm thick red mud, red mud:$Bi_2O_3$, red mud:$Ba(OH)_2$ and red mud:$Bi_2O_3$:$Ba(OH)_2$ samples are found to possess the attenuation equivalent to 180 mm lead at 1.33 MeV. The HVL of the sample at 150 kVp is found to be 3.10 mm, 0.7434 mm, 1.0754 mm and 0.8776 mm for red mud, red mud:$Bi_2O_3$, red mud:$Ba(OH)_2$ and red mud:$Bi_2O_3$:$Ba(OH)_2$ sample, respectively. The red mud, red mud:$Bi_2O_3$, red mud:$Ba(OH)_2$ and red mud:$Bi_2O_3$:$Ba(OH)_2$ samples possess the compressive strength of 34.18 MPa, 282.15 MPa, 144 MPa and 122 MPa, respectively. This material can be used to build radiation shielding structures in medical diagnosis, radiotherapy, industrial radiography, particle accelerators, food sterilization plants, nuclear power plants, and radioactive material storage rooms without further structural support unlike lead (concrete walls).

In the present invention, iron rich red mud is converted into X- and gamma-ray shielding material in a green manner. Red mud is an alumina industrial waste and is left unused in the disposal plants due to inadequate technologies for large scale utilization. It is hazardous due to its extreme alkalinity (>11 pH). The developed material is lead free and economically viable. Moreover, the material consumes less space compared to lead (lead need additional support structures), heavy weight and light weight concretes based radiation shields. It can be used to protect common public, operating personals and environment from harmful X- and gamma-rays, which can emerge out of medical therapy, nuclear power plants, food sterilization plants, radioactive nuclide storage rooms, particle accelerators, and industrial radiography. The red mud based radiation shields will be much cheaper than lead and heavy weight concrete as it is based on industrial waste. Utilization of such secondary resources will reduce primary mining, accumulation of hazardous waste and associated environmental pollution and deforestation.

Figure 2:
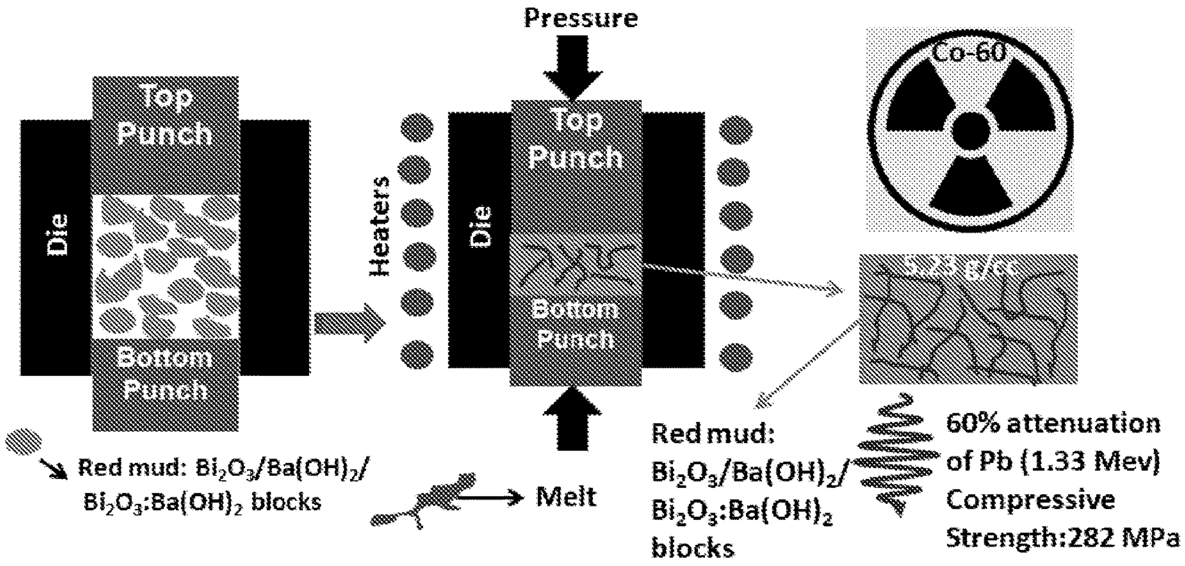
FIG. 2: Schematic diagram of fabrication of high dense red mud based radiation shielding blocks.
Figure 3:
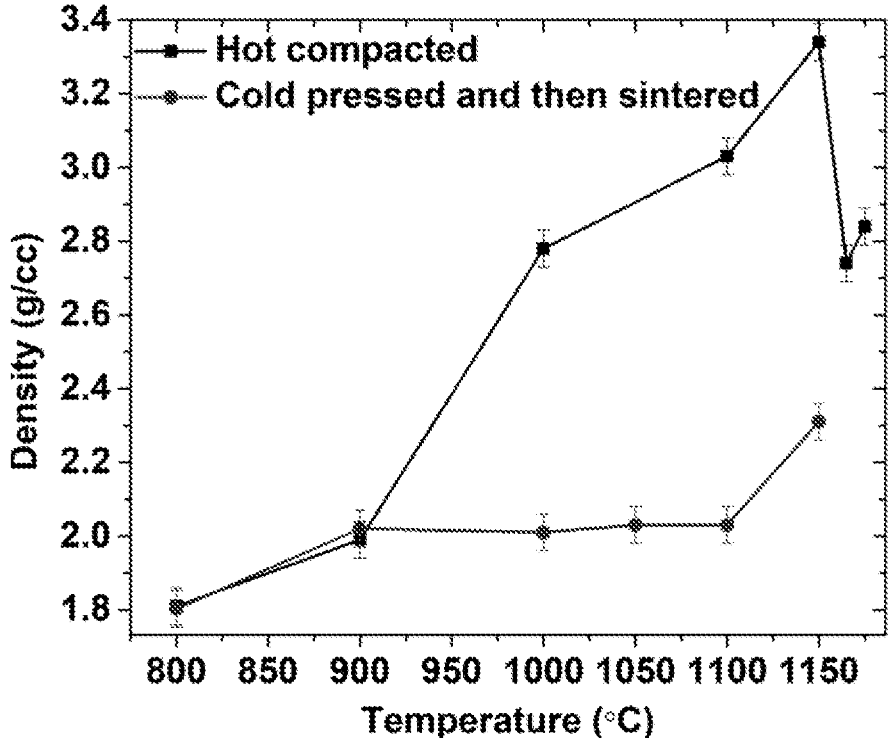
FIG. 3: Comparing the density of pure red mud pellet hot pressed and cold pressed and sintered at various temperature. The hot press and cold press sample was compacted by applying 23.4 and 53.14 MPa, respectively.

Thus, the present application provides a green and eco-friendly method for the conversion of hazardous red mud into X- and $\gamma$-rays shielding materials. The process is schematically illustrated in FIGS. 1 and 2. The as-collected red mud was dried at 90° C. in a hot air oven for 15 hrs and then ball milled for 2 hrs to crush them into fine powders. 50 wt % of $Bi_2O_3$ or $Ba(OH)_2$ or the mixture of 25 wt % $Bi_2O_3$ and 25 wt % of $Ba(OH)_2$ were added to the ball milled red mud and then the mixture was again ball milled for one hour to have uniform mixture. Appropriate amount of the grinded red mud or red mud:$Bi_2O_3$ or red mud:$Ba(OH)_2$ or red mud:$Bi_2O_3$:$Ba(OH)_2$ mixture was taken in an appropriate die. The die loaded with red mud, red mud:$Bi_2O_3$, red mud:$Ba(OH)_2$, red mud:$Bi_2O_3$:$Ba(OH)_2$ was heated to 1150° C., 1000° C., 1050° C. and 1000° C., respectively with the heating rate of 7° C./min. After dwelling for ≈30 minutes, the red mud, red mud:$Bi_2O_3$, red mud:$Ba(OH)_2$ and red mud:$Bi_2O_3$:$Ba(OH)_2$ samples were compacted by applying 23.4 MPa, 40 MPa, 23.4 MPa and 40 MPa pressure, respectively. The compacted samples were then cooled with the rate of 10° C./min. This process resulting in the decomposition of boehmite, goethite, gibbsite, calcite and $Ba(OH)_2$ and formation of new phases like hematite, cancrinite, nepheline, pseudobrookite, gehlenite, silico-ferrite of calcium and aluminum (SFCA), $Bi_{12}SiO_{20}$, $2BiFeO_3$, $BaTiO_3$, $BaFe_{12}O_{19}$, etc., were observed. The density of red mud, red mud:$Bi_2O_3$, red mud:$Ba(OH)_2$ and red mud:$Bi_2O_3$:$Ba(OH)_2$ blocks are 3.3, 5.23, 4.6 and 4.7 g/cc, respectively. The porosity of the developed red mud, red mud:$Bi_2O_3$, red mud:$Ba(OH)_2$ and red mud:$Bi_2O_3$:$Ba(OH)_2$ blocks are 3.8%, 2.8%, 0.08% and 2.0%, respectively.

Further, the gamma ray attenuation coefficients of the samples were studied using Co-60 source. The half value layer of red mud, red mud:$Bi_2O_3$, red mud:$Ba(OH)_2$ and red mud:$Bi_2O_3$:$Ba(OH)_2$ sample was found to be 34.02 mm, 20.96 mm, 26.80 mm, and 24.0 mm, respectively at 1.33 MeV.

Furthermore, the X-ray attenuation of the developed samples was studied using 150 kVp X-rays. The half value layer of the red mud, red mud:$Bi_2O_3$, red mud:$Ba(OH)_2$ and red mud:$Bi_2O_3$:$Ba(OH)_2$ sample was found to be 3.10 mm, 0.7434 mm, 1.0754 mm and 0.8776 mm, respectively at 150 kVp. Table 1 provides the Half value layer of the hot pressed materials at various kVp.

The compressive strength of the samples were tested as per ASTM C39 standard and the red mud, red mud:$Bi_2O_3$, red mud:$Ba(OH)_2$ and red mud:$Bi_2O_3$:$Ba(OH)_2$ samples possess compressive strength of 34.18 MPa, 282.15 MPa, 144 MPa and 122 MPa, respectively.

Since red mud, red mud:$Bi_2O_3$, red mud:$Ba(OH)_2$ and red mud:$Bi_2O_3$:$Ba(OH)_2$ blocks possess sufficient strength as well as X- and gamma ray attenuation, it can be used to build the radiation shielding structure in medical diagnostic, medical therapy, industrial radiography, particle accelerators, food sterilization plant, storage room for radioactive materials, and nuclear power plants, without additional structural support unlike lead.

TABLE 1

Half value layer of the hot pressed samples.

| Sample | HVL (±0.03 mm) | | | HVL (±0.5 mm) |
|---|---|---|---|---|
| | 100 kVp | 125 kVp | 150 kVp | 1.33 MeV |
| red mud | 2.177 | 2.70348 | 3.10 | 34.02 |
| red mud:$Bi_2O_3$ | 0.66524 | 0.70562 | 0.7434 | 20.96 |
| red mud:$Ba(OH)_2$ | 0.81829 | 0.92968 | 1.075 | 26.80 |
| red mud:$Bi_2O_3$:$Ba(OH)_2$ | 0.74108 | 0.79956 | 0.8776 | 24.00 |

EXAMPLES

The following example is given by way of illustration of the working of the invention in actual practice and therefore should not be construed to limit the scope of the present invention.

Example 1

Red mud was collected and dried in hot-air oven at 90° C. for 15 hrs. 2 kg red mud was grinded in a ball mill for 4 hrs using six numbers of 350 gm stainless steel balls. Red mud was taken in a 50 mm die in which the interior wall of the die and the bottom and top plungers were coated with molybdenum as lubricant. The sample along with the die was loaded in a hot press and then heated to 1150° C. with the rate of 7° C./min. 23.4 MPa pressure was applied after 30 minutes of dwelling at 1150° C. Subsequently, the sample was cooled with the rate of 10° C./min. The density and porosity of the developed block are 3.3 g/cc and 3.8%, respectively. The red mud blocks with various thicknesses ranging from 1-60 mm were fabricated and then the gamma ray attenuation of the samples were studied using Cobalt-60 source.

The gamma ray attenuation characteristics of the samples were studied using Cobalt-60 ($^{60}Co$) source (activity=1 μCi). The intensity of the direct and the transmitted beams were recorded using Barium Fluoride scintillation detector ($BaF_2$) with the Multi-Channel Analyzer. The bias voltage is 1400 V. The spectra were readout using Epsilon software and the area under the photopeak of 1.33 and 1.17 MeV was integrated using the apple software. The measured spectra were converted from channel number to energy by calibrating using various gamma energy sources like $^{60}Co$(1.17 and 1.33 MeV), $^{22}Na$(0.511 and 1.274 MeV), and $^{137}Cs$ (0.662 MeV). This calibration was done every two to three hours of measurement. Source and detector distance was 150 mm. The Half Value Layer (HVL) (i.e., thickness required to attenuate the incoming radiation by 50%) of the samples were determined by varying the thickness of the samples. The half value layer (HVL) of the developed sample was 34.02 mm at 1.33 MeV.

The X-ray attenuation of shields were determined at various kVp. X-ray machine (Ultisys 52, kV range 40-150 kVp, mA range 10-640 mA) was used as an X-ray source. The residual X-ray that passes through the tile was determined using X2 R/F Sensor at different accelerating voltages. The IEC 61331-1 quality beam was produced by increasing the Al filter stepwise at the tube head. The recommended HVL of Al at 120 kVp is 4.13 mm. All the measurements were done with a 2.64 mm aluminium added filter. The distance between the sample and the X-ray focal spot is one meter. Linear attenuation coefficient (μ) and half value layer (HVL) were calculated using the equation 1 and 2, respectively.

$$I = I_o e^{\mu d} \quad \text{eq. (1)}$$

$$HVL = 0.693/\mu \quad \text{eq. (2)}$$

Where, $I_o$ & I are the intensity of direct and transmitted X-rays, respectively, μ is the linear attenuation coefficient and d is the thickness of the shield.

The HVL of the sample at 100 kVp, 125 kVp and 150 kVp X-ray is 2.177 mm, 2.7034 mm and 3.10 mm, respectively. The compressive strength of the sample was studied as per ASTM C39 standard. The developed sample possess the compressive strength of 34.18 MPa, which is suitable for civil constructions.

The leaching of heavy elements from the sintered tiles was determined using Toxicity Characteristic Leaching Procedure (TCLP) as described in ASTM D3987. The eluate was collected from leachant after 1, 7 & 28 days and the presence of toxic elements like Cd, Cr, Pb, etc., in the eluate, was determined in ppm level using Atomic Absorption Spectrometer (Thermo Scientific iCE3500 series). No heavy elements were found to leach from the shield.

Example 2

The red mud was collected and dried in hot-air oven at 90° C. for 15 hrs. 2 kg red mud was grinded in a ball mill for 4 hrs using six numbers of 350 gm stainless steel balls. Subsequently 2 kg $Bi_2O_3$ was added to the grinded red mud and then the mixture was further grinded for one hour for uniform mixing. The grinded red mud:$Bi_2O_3$ mixture was taken in a 50 mm graphite die. The interior wall of the die and the bottom and top plunger was coated with molybdenum. The sample along with die was loaded in a hot press and then heated to 1000° C. with the rate of 7° C./min. 39 MPa pressure was applied in a hot press after 25 minutes of dwelling at 1000° C. Subsequently, the sample was cooled with the rate of 10° C./min. The density and porosity of the developed sample was 5.23 g/cc and 2.8%, respectively. The radiation shielding blocks with various thicknesses ranging from 4-60 mm were developed and then the gamma ray attenuation of the samples was studied using Cobalt-60 source. The half value layer (HVL) of the developed sample is 20.96 mm at 1.33 MeV. The HVL of the sample at 100 kVp, 125 kVp and 150 kVp X-ray is 0.6652 mm, 0.7056 and 0.7434 mm, respectively. The compressive strength of the samples was studied as per ASTM C39. The developed sample possess the compressive strength of 282.18 MPa and no heavy elements were found to leach from the shield.

Example 3

Red mud was collected and dried in hot-air oven at 90° C. for 15 hrs. 2 kg red mud was grinded in a ball mill for 4 hrs using six numbers of 350 gm stainless steel balls. 2 kg $Ba(OH)_2$ was added to the grinded red mud and then the mixture was further grinded for an hour to have uniform mixture. The grinded red mud:$Ba(OH)_2$ mixture was taken in a 50 mm graphite die. The interior wall of the die and the bottom and top plungers were coated with molybdenum as high temperature lubricant. The sample along with die was loaded in a hot press and then heated to 1050° C. with the rate of 7° C./min. 23.4 MPa pressure was applied in a hot press after 30 minutes of dwelling at 1050° C. Subsequently, the sample was cooled with the rate of 10° C./min. The density and porosity of the developed sample was 4.6 g/cc and 0.08%, respectively. The radiation shielding blocks with various thicknesses ranging from 1.5-50 mm thick samples were fabricated and then the gamma ray attenuation of the samples were studied using Cobalt-60 source. The half value layer (HVL) of the developed sample was 26.80 mm at 1.33 MeV. The HVL of the sample at 100 kVp, 125 kVp and 150 kVp X-ray is 0.8182 mm, 0.9297 and 1.0754 mm, respectively. The compressive strength of the samples was studied as per ASTM C39 standard. The developed sample possess the compressive strength of 144 MPa, which is suitable for civil constructions. No heavy elements were found to leach from the developed shield.

Example 4

The red mud was collected and dried in hot-air oven at 90° C. for 15 hrs. 2 kg red mud was grinded in a ball mill for 4 hrs using six numbers of 350 gm stainless steel balls. Subsequently 1 kg $Ba(OH)_2$ and 1 kg $Bi_2O_3$ was added to the grinded red mud and then the mixture was further grinded for one hour for uniform mixing. The grinded red mud:Ba $(OH)_2$:$Bi_2O_3$ mixture was taken in a 50 mm graphite die. The interior wall of the die and the bottom and top plunger was coated with molybdenum as high temperature lubricant. The sample along with die was loaded in a hot press and then heated to 1000° C. with the rate of 7° C./min. 39 MPa pressure was applied in a hot press after 35 minutes of dwelling at 1000° C. Subsequently, the sample was cooled with the rate of 10° C./min. The density and porosity of the developed sample was 4.7 g/cc and 2.0%, respectively. The radiation shielding blocks with various thicknesses ranging from 1.5-60 mm were developed and then the gamma ray attenuation of the sample was studied using Cobalt-60 source. The half value layer (HVL) of the developed sample is 24 mm at 1.33 MeV. The HVL of the sample at 100 kVp, 125 kVp and 150 kVp X-ray is 0.74108 mm, 0.7996 and 0.8776 mm, respectively. The compressive strength of the sample was studied as per ASTM C39. The developed sample possess the compressive strength of 122 MPa, which is suitable for civil constructions. No heavy elements were found to leach from the shield.

Example 5

The red mud was collected and dried in hot-air oven at 90° C. for 15 hrs. 2 kg red mud was grinded in a ball mill for 4 hrs using six numbers of 350 gm stainless steel balls. The grinded red mud was taken in a 60 mm hot die steel die. The samples with various thicknesses ranging from 5 mm till 80 mm were fabricated by applying 72 MPa pressure. The developed blocks were sintered at 1150° C. for 30 minutes in a muffle furnace with the heating rate of 7° C./min. Then the samples were cooled to room temperature with the rate of 10° C./min. The density and porosity of the developed samples are 2.13 g/cc and 13%, respectively. The gamma ray attenuation of the sample was studied using Cobalt-60 source. The half value layer (HVL) of the developed sample was found to be 49 mm at 1.33 MeV. The compressive strength of the sample was 20 MPa.

Example 6

Red mud was collected and dried in hot-air oven at 90° C. for 15 hrs. 2 kg red mud was grinded in a ball mill for 4 hrs using six numbers of 350 gm stainless steel balls. Further 2 kg $Bi_2O_3$ was mixed with grinded red mud and then the mixture was ball milled for another one hour for uniform mixing. The above mixture was taken in a 60 mm hot die steel die. The samples with various thicknesses ranging from 5 mm till 80 mm were fabricated by applying 72 MPa pressure. The developed blocks were sintered at 1000° C. for 25 minutes with the heating rate of 7° C./min. Then the samples were cooled to room temperature with the cooling rate of 10° C./min. The density and the porosity of the developed block are 2.6 g/cc and 47%, respectively. The gamma ray attenuation of the samples was studied using Cobalt-60 source. The half value layer (HVL) of the developed sample at 1.33 MeV is 40 mm. The compressive strength of the samples is 18 MPa.

Example 7

The red mud was collected and dried in hot-air oven at 90° C. for 15 hrs. 2 kg red mud was grinded in a ball mill for 4 hrs using six numbers of 350 gm stainless steel balls. Further 2 kg $Ba(OH)_2$ was mixed with grinded red mud and then the mixture was ball milled for another one hour for uniform mixing. The red mud:$Ba(OH)_2$ mixture was taken in a 60 mm hot die steel die. The samples with various thicknesses ranging from 5 mm till 80 mm were fabricated by applying 72 MPa pressure. The developed blocks were sintered at 1050° C. for 30 minutes with the heating rate of 7° C./min. Then the samples were cooled to room temperature with the cooling rate of 10° C./min. The density and the porosity of the developed blocks are 1.9 g/cc and 40%, respectively. The gamma ray attenuation of the samples were studied using Cobalt-60 source. The half value layer (HVL) of the developed sample at 1.33 MeV is 54 mm. The compressive strength of the sample is 7 MPa.

Example 8

The red mud was collected and dried in hot-air oven at 90° C. for 15 hrs. 2 kg red mud was grinded in a ball mill for 4 hrs using six numbers of 350 gm stainless steel balls. Further 1 kg $Ba(OH)_2$ and 1 kg $Bi_2O_3$ was added with grinded red mud and then the mixture was ball milled together for another one hour for uniform mixing. The red mud:$Bi_2O_3$:$Ba(OH)_2$ mixture was taken in a 60 mm hot die steel die. The samples with various thicknesses ranging from 5 mm till 80 mm were fabricated by applying 72 MPa pressure. The developed blocks were sintered at 1000° C. for 30 minutes with the heating rate of 7° C./min. Then the samples were cooled to room temperature with the rate of 10° C./min. The density and porosity of the developed blocks are 2.3 g/cc and 43.7%, respectively. The gamma ray attenuation of the samples was studied using Cobalt-60 source. The half value layer (HVL) of the developed sample is 46 mm at 1.33 MeV. The compressive strength of the sample is 18 MPa.

Table 2 provides the details of the required thickness of the shield for various composition at 150 kVp and at 1.33 MeV (Co-60 Source).

TABLE 2

| | | | | 150 KVp | | | Cobalt 60 | | |
|---|---|---|---|---|---|---|---|---|---|
| Sample | Red Mud (%) | $Bi_2O_3$ (%) | $Ba(OH)_2$ (%) | Attenuation Coefficient (±0.002 $mm^{-1}$) | HVL (±0.03 mm) | 2.5 mm Lead Equivalent (±0.25 mm) | Attenuation Coefficient (±0.0008 $mm^{-1}$) | HVL (±0.5 mm) | 180 mm Lead Equivalent (±4 mm) |
| red mud | 100 | — | — | 0.224 | 3.10 | 25.81 | 0.02037 | 34.02 | 489.88 |
| red mud: $Bi_2O_3$ | 40 | 60 | — | 1.059 | 0.65 | 5.46 | — | — | — |
| | 50 | 50 | — | 0.932 | 0.74 | 6.20 | 0.03306 | 20.96 | 301.82 |
| | 60 | 40 | — | 0.725 | 0.96 | 7.97 | — | — | — |
| | 70 | 30 | — | 0.566 | 1.22 | 10.20 | — | — | — |
| red mud:$Ba(OH)_2$ | 40 | — | 60 | 0.661 | 1.05 | 8.74 | — | — | — |
| | 50 | — | 50 | 0.644 | 1.075 | 8.96 | 0.02586 | 26.80 | 385.92 |
| | 60 | — | 40 | 0.571 | 1.21 | 10.11 | — | — | — |
| | 70 | — | 30 | 0.515 | 1.35 | 11.21 | — | — | — |
| red mud:$Bi_2O_3$:$Ba(OH)_2$ | 50 | 25 | 25 | 0.790 | 0.877 | 7.31 | 0.029 | 24 | 345.6 |
| | 50 | 35 | 15 | 0.776 | 0.89 | 7.44 | — | — | — |
| | 50 | 15 | 35 | 0.764 | 0.90 | 7.56 | — | — | — |

The main advantages of the present invention are:

The developed red mud shields of the present application are advantageous due to following reasons:

1. This novel technique paves the way for conversion of hazardous red mud into X- and γ-ray shielding material, which can be used as an alternative of toxic lead and heavy weight concrete in a building sectors to fabricate X- and γ-ray shielding structures.
2. This technique helps to close the pores tremendously and thereby to achieve high dense red mud blocks having density ≈5.2 g/cc, which is much higher than the red mud/industrial waste based radiation shield reported so far.
3. The material is lead free and the process is green as it does not release any greenhouse gases like $SO_2$ and $CO_2$ during sintering.
4. The diffusion bonded red mud:$Bi_2O_3$, red mud:$Ba(OH)_2$ and pure red mud sample possess 60%, 46.6% and 37% of the attenuation of lead at 1.3 MeV gamma rays (Cobalt-60), respectively.
5. The HVL of pure red mud block (34.02 mm) is nearly half of light weight concrete (60.5 mm) at 1.33 MeV and possess sufficient strength (34.18 MPa) for building applications. So, it is highly economically viable and occupies less space than the conventional concrete.
6. The developed material possess the compressive strength of 34-282 MPa, which is higher than the common bricks and concrete. So, the developed blocks can be used to build the radiation shielding structures without any additional structural support unlike lead.
7. The HVL is nearly 3 times less than the already reported red mud based radiation shielding materials.
8. The developed shields will be cheaper than lead, since it uses industrial waste as one of the major raw material. It will reduce the usage of toxic lead for radiation shielding applications.
9. It will generate values to the red mud and will reduce its accumulation and associated environmental problems like soil, air and ground water pollution.
10. It will occupy less space than lead (need additional support structure), heavy weight and light weight concrete.
11. The developed material is thermally stable until 1000° C., so its life will be higher than the concrete and polymer based radiation shielding materials.

We claim:

1. A red mud based material for attenuation of x-rays and gamma rays, the red mud based material comprising:

(a) from 50 wt % to 100 wt % red mud; and (b) from 0 to 50 wt % of:

(i) $Bi_2O_3$; or (ii) $Ba(OH)_2$; or (iii) a 50:50 wt % mixture of $Bi_2O_3$ and $Ba(OH)_2$, wherein the red mud based material has one or more of a density of from 3.3 g/cc to 5.23 g/cc, a compressive strength of from 34 MPa to 282.15 MPa, or a half value layer from 20.96 mm to 34.02 mm at 1.33 MeV.

2. The red mud based material of claim 1, wherein the density of the red mud based material is from 3.3 g/cc to 5.23 g/cc.

3. The red mud based material of claim 1, selected from:
red mud having a density of 3.3 g/cc; or
red mud:$Bi_2O_3$ having a density of 5.23 g/cc; or
red mud:$Ba(OH)_2$ having a density of 4.6 g/cc; or
red mud:$Bi_2O_3$:$Ba(OH)_2$ having a density of 4.7 g/cc.

4. The red mud based material of claim 1, wherein the compressive strength of the material is from 34 MPa to 282.15 MPa.

5. The red mud based material of claim 1, selected from:
red mud having a compressive strength of 34.18 MPa; or
red mud:$Bi_2O_3$ having a compressive strength of 282.15 MPa; or
red mud:$Ba(OH)_2$ having a compressive strength of 144 MPa; or
red mud:$Bi_2O_3$:$Ba(OH)_2$ having a compressive strength of 122 MPa.

6. The red mud based material of claim 1, wherein the half value layer of the material is from 20.96 mm to 34.02 mm at 1.33 MeV ($^{60}Co$ source).

7. The red mud based material of claim 1, wherein the half value layer of the material at 150 kVp X-ray is from 0.7434 mm to 3.10 mm.

8. A process for preparation of a red mud based material for attenuation of x-rays and gamma rays, the process comprising:
(a) taking 50 wt % to 70 wt % of red mud;
(b) separately taking 30 to 50 wt % of a component chosen from:
(i) $Bi_2O_3$; or
(ii) $Ba(OH)_2$; or
(iii) a 50:50 wt % mixture of $Bi_2O_3$ and $Ba(OH)_2$;
(c) grinding the red mud in a ball mill for 4 hours;
(d) adding to the ball mill of (c) the component of (b) and grinding for one hour to obtain a mixture;
(e) taking the mixture obtained in (d) in a graphite die and sintering at a temperature from 1000° C. to 1150° C. in a hot press at a heating rate of 7° C./min to obtain a partially melted mixture; and
(f) compacting the partially melted mixture obtained in (e) by applying pressure of from 23 MPa to 40 MPa for 30 seconds to 60 seconds and cooling at a rate of 10° C./minute to 27° C. to obtain the red mud based material.

9. The process of claim 8, wherein the sintering results in formation of highly dense phases selected from $Fe_3O_4$, hematite, cancrinite, nepheline, pseudobrookite, gehlenite, silico-ferrite of calcium and aluminum (SFCA), $Bi_{12}SiO_{20}$, $2BiFeO_3$, $BaTiO_3$, and $BaFe_{12}O_{19}$.

10. A process for preparation of a red mud based material, the process comprising:
(a) milling a red mud to form a milled red mud;
(b) combining the milled red mud with $Bi_2O_3$, $Ba(OH)_2$, or a mixture thereof to form a red mud mixture, wherein the red mud mixture comprises from 50 to 70 wt. % of the milled red mud and from 30 to 50 wt. % of a combined weight of components $Bi_2O_3$ and $Ba(OH)_2$;
(c) sintering the red mud mixture obtained in (b) at a temperature from 1000° C. to 1150° C. to obtain a partially melted mixture;
(d) compacting the partially melted mixture obtained in (c) by applying pressure of from 23 MPa to 40 MPa to obtain the red mud based material; and
(e) cooling the red mud based material.

11. The process of claim 10, wherein the pressure is applied to the partially melted mixture for 30 seconds to 60 seconds.

12. The process of claim 8, wherein the red mud based material has one or more of a density of from 3.3 g/cc to 5.23 g/cc, a compressive strength of from 34 MPa to 282.15 MPa, or a half value layer from 20.96 mm to 34.02 mm at 1.33 MeV.

13. The process of claim 10, wherein the cooled red mud based material has one or more of a density of from 3.3 g/cc to 5.23 g/cc, a compressive strength of from 34 MPa to 282.15 MPa, or a half value layer from 20.96 mm to 34.02 mm at 1.33 MeV.

* * * * *